United States Patent [19]

Trani

[11] 3,979,408
[45] Sept. 7, 1976

[54] 2-(PYRROL-1-YL)AMINO-4,5-DIHYDRO-1H-IMIDAZOLE DERIVATIVES

[75] Inventor: Aldo Trani, Milan, Italy

[73] Assignee: Gruppo Lepetit S.p.A., Milan, Italy

[22] Filed: May 24, 1974

[21] Appl. No.: 473,038

[30] Foreign Application Priority Data

May 25, 1973 United Kingdom............ 25129/73

[52] U.S. Cl................. 260/309.6; 260/256.4 N; 424/251; 424/273
[51] Int. Cl.²................................. C07D 49/34
[58] Field of Search................ 260/309.6, 256.4 N

[56] References Cited
UNITED STATES PATENTS

| 3,501,487 | 3/1970 | Poos | 260/309.6 |
| 3,850,926 | 11/1974 | Stähle et al. | 260/309.6 X |
| 3,860,596 | 1/1975 | Kim et al. | 260/256.4 N |
| 3,892,554 | 7/1975 | Schneider | 260/256.4 N |

OTHER PUBLICATIONS

Mosby, Journ. Chem. Soc., pp. 3997–4003 (1957).
Rio et al., Bull'n Soc. Chim. France, No. 5, 1971, pp. 1723–1727.
Najer et al., C.A. 4647c.
Popelak et al., C.A. 16628d.

Primary Examiner—Ethel G. Love
Attorney, Agent, or Firm—Theodore Post; C. Kenneth Bjork

[57] ABSTRACT 2-(Pyrrol-1-yl)amino-4,5-dihydro-1H-imidazole derivatives of the following general formula I

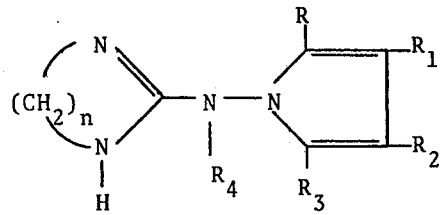

wherein R, $R_1$, $R_2$ and $R_3$ may be the same or different and are independently selected from the class consisting of hydrogen, lower alkyl, carbo-lower alkoxy, phenyl, substituted phenyl, $R_4$ represents hydrogen or lower alkyl, n is an integer and may be 2 or 3. The corresponding pharmaceutically acceptable acid addition salts of the substances of formula I above are considered as a part of the invention. The invention compounds display very interesting antihypertensive properties.

3 Claims, No Drawings

2-(PYRROL-1-YL)AMINO-4,5-DIHYDRO-1H-IMIDAZOLE DERIVATIVES

SUMMARY OF THE INVENTION

The present invention relates to new antihypertensive compounds. More particularly the substances with which the invention is concerned are 2-(pyrrol-1-yl)amino-4,5-dihydro-1H-imidazole derivatives of the following general formula I

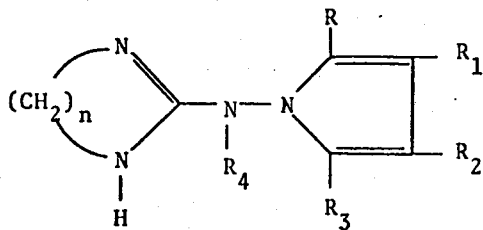

wherein R, $R_1$, $R_2$, $R_3$ may be the same or different and are independently selected from the class consisting of hydrogen, lower alkyl, carbo-lower alkoxy, phenyl, substituted phenyl, $R_4$ represents hydrogen or lower alkyl, n is an integer and may be 2 or 3. Also the pharmaceutically acceptable acid addition salts of the compounds of the formula I are an object of the present invention. Representative of such salts are mineral acid salts, for instance, the hydrochloride, hydrobromide, sulfate, phosphate and the like, and the organic acid salts, such as the oxalate, maleate, succinate, acetate, p-toluenesulfonate, cyclohexanesulfonate and the like.

As it is intended in the specification and claims, the terms "lower alkyl" and "lower alkoxy" designate straight or branched aliphatic alkyl or alkoxy moieties having a minimum of one and a maximum of four carbon atoms, whereas the term "substituted phenyl" essentially refers to phenyl substituted with lower alkyl and nitro groups.

The general procedure for preparing the compounds according to the invention comprises reacting a hydrazino compound of the formula II

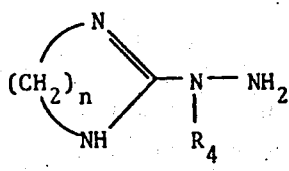

or an acid addition salt thereof, with a 1,4-dicarbonyl compound of the formula III

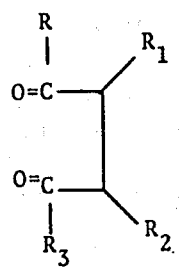

or a functional derivative thereof wherein R, $R_1$, $R_2$, $R_3$, $R_4$ and n have the meanings given above.

The reactants are allowed to contact in about equimolecular amounts, though an excess of the compound of the formula III or of an acid addition salt thereof may be sometimes advantageously employed. The reaction is generally carried out in the presence of a solvent, which may be selected from $C_1$–$C_4$ lower alkanols, anhydrous benzene, tetrahydrofuran and the like, or mixtures thereof. Preferred solvents are ethanol and mixtures of ethanol and anhydrous benzene. Catalytic amounts of glacial acetic acid are added to speed up the cyclization step and in some instances acetic acid is also employed as the reaction solvent.

The reaction is performed at a temperature higher than 35°C, preferably at the boiling temperature of the solvent, and is complete within a range of time from about 5 to about 40 hours. Then the products are recovered following procedures which are entirely known to a skilled chemist.

For instance, the reaction mixture may be concentrated to small volume by evaporating off the solvent and the obtained solid residue may be purified by column cromatography or by crystallization from a suitable solvent.

Also the acid addition salts of the compounds of the above formula I are prepared through well known procedures.

Thus, for instance, they may be directly obtained if the cyclization reaction is carried out by using as the starting material an acid addition salt of the compounds of the formula II. Alternatively, if at the end of the cyclization step the compound I is present as a free base, a suitable amount of one of the above mentioned inorganic or organic acids can be added to the reaction medium, so that the corresponding acid addition salt is readily recovered. In some cases, it may be convenient to synthesize first the acid salt of the compound of formula I and then, to set free the corresponding base by usual procedures. The hereindescribed substances are solid and generally high-melting compounds, very soluble in water, aqueous diluted mineral acids and $C_1$–$C_4$ lower alkanols.

As stated above, the compounds according to the invention are endowed with very good antihypertensive properties. The pharmacological tests for evaluating this activity were carried out on conscious normotensive and hypertensive mongrel dogs of both sexes. The compounds were administered orally or intravenously, and an account of the antihypertensive effectiveness was obtained by measuring the decrease of the blood pressure. In representative experiments it was found that amounts of about 5 mg/kg. of 2-(2,5-dimethyl-pyrrol-1-yl)amino-4,5-dihydro-1H-imidazole administered per os were responsible of a diminution of the blood pressure of about 60%.

These very good biological properties are coupled with a surprisingly low toxicity, since the $LD_{50}$ values are generally higher than 1000 mg/kg. p.o. in mice. It can be easily noticed, therefore, that the present invention is concerned with very promising antihypertensive agents, having a very favorable therapeutic index, expressed as a ratio between the $LD_{50}$ and $ED_{50}$ values.

Accordingly the present invention provides a therapeutic composition comprising as the active ingredient a compound of the invention together with a pharmaceutically acceptable carrier.

The following Examples are given for purposes of illustration only, but are not intended to establish any limit to the invention. They describe in detail some representative compounds of the invention and the process for their manufacture.

DESCRIPTION OF THE PREFERRED EMBODIMENTS

EXAMPLE 1

2-(2,5-Dimethyl-pyrrol-1-yl)amino-4,5-dihydro-1H-imidazole maleate.

To a boiling solution of 8.63 g. (0.0756 mole) of 2,5-hexanedione in 50 ml. of absolute ethanol, a solution of 14 g. (0.0614 mole) of 2-hydrazino-4,5-dihydro-1H-imidazole hydroiodide and 3.47 g. (0.0620 mole) of potassium hydroxide in 120 ml. of absolute ethanol and 60 ml. of anhydrous benzene is quickly added. The mixture is stirred under reflux for 30 minutes and at room temperature for 12 hours. The potassium iodide which forms is cast off by filtration, then the mixture is concentrated to small volume by evaporating off the solvent. A residue is obtained which is dissolved with methylene chloride. To the obtained solution an ether solution of maleic acid is added and a precipitate readily forms, which is recrystallized two times from absolute ethanol. Yield 1.3 g. M.p. 177°–8°C. The free base melts at 192°–3°C (from methanol).

EXAMPLE 2

2-(2,3,5-Trimethyl-pyrrol-1-yl)amino-4,5-dihydro-1H-imidazole oxalate.

The title compound is obtained by operating substantially as in the previous example, starting from 21 g. (0.164 mole) of 3-methyl-2,5-hexanedione and 28 g. (0.160 mole) of 2-hydrazino-4,5-dihydro-1H-imidazole hydrobromide, and adding at the end of the reaction an ether solution of oxalic acid. Yield 6.6 g. M.p. 188°–9°C (from isopropanol).

EXAMPLE 3

2-(3,4-Dicarbethoxy-2,5-dimethyl-pyrrol-1-yl)amino-4,5-dihydro-1H-imidazole hydrobromide.

To a solution of 15 g. (0.0581 mole) of diethyl 2,3-diacetylsuccinate in 150 ml. of absolute ethanol, 1.2 ml. of glacial acetic acid is added. The mixture is gently refluxed for 5 minutes then 8.13 g. (0.0467 mole) of 2-hydrazino-4,5-dihydro-1H-imidazole hydrobromide is added. The mixture is refluxed for 20 hours, then the solvent is evaporated off. The obtained residue is recrystallized several times from isopropanol, and 6.3 g. of the title compound are recovered. M.p. 172°–4°C.

EXAMPLE 4

2-(3,4-Dicarbethoxy-2,5-diethyl-pyrrol-1-yl)amino-4,5-dihydro-1H-imidazole hydrobromide.

The compound is obtained following substantially the method described in Example 3, by reacting 13 g. (0.0455 mole) of diethyl-2,3-dipropionyl-succinate with 8.14 g. (0.0449 mole) of 2-hydrazino-4,5-dihydro-1H-imidazole hydrobromide. Yield 55 g. M.p. 181°–2°C (from isopropanol/diethyl ether). The free base melts at 155°C (from diethyl ether).

EXAMPLE 5

2-(2,5-Di-isopropyl-pyrrol-1-yl)amino-4,5-dihydro-1H-imidazole

The title compound is obtained as the free base by reacting 3.92 g. (0.0230 mole) of 2,7-dimethyl-3,6-octane-dione with 4.16 g. (0.0230 mole) of 2-hydrazino-4,5-dihydro-1H-imidazole hydrobromide according to the same procedure of Example 3, and adding at the end of the reaction a 10% aqueous solution of sodium hydroxide. Yield 2.5 g. M.p. 230°–32°C (from diethyl ether).

EXAMPLE 6

2-(Pyrrol-1-yl)amino-4,5-dihydro-1H-imidazole.

By reacting 3.7 g. (0.0280 mole) of 2,5-dimethoxy-tetrahydrofuran with 5 g. (0.0276 mole) of 2-hydrazino-4,5-dihydro-1H-imidazole hydrobromide according to the process reported in Example 3, and adding at the end of the reaction a 10% aqueous solution of sodium hydroxide, the title compound is obtained as the free base. Yield 1.5 g. M.p. 183°–4°C. (from acetone.) The maleate melts at 142°–5°C (from acetone).

EXAMPLE 7

2-[2,5-Bis-(m-nitrophenyl)-pyrrol-1-yl]amino-4,5-dihydro-1H-imidazole hydrochloride.

A solution of 6 g. (0.0302 mole) of 2-hydrazino-4,5-dihydro-1H-imidazole hydrobromide and 10 g. (0.0331 mole) of 1,2-bis-(m-nitrobenzoyl)-ethane in 700 ml. of glacial acetic acid is refluxed for 30 hours. After cooling, the reaction mixture is filtered and the obtained residue is suspended in hot benzene. The benzene solution is filtered, the residue is dissolved with water and upon addition of ammonia a precipitate readily forms. This precipitate is dissolved with a mixture of chloroform and ethanol, then a 10% aqueous solution of hydrochloric acid is added. A solid separates, which is collected and recrystallized from a mixture of water and methanol to give 1.65 g. of the title compound. M.p. 305°C.

EXAMPLE 8

2-[2,5-Bis-(p-tolyl)-pyrrol-1-yl]amino-4,5-dihydro-1H-imidazole hydrochloride.

The compound of the title is prepared substantially as described in Example 7, starting from 30 g. (0.108 mole) of 1,2-bis-(p-toluyl)-ethane and 17.92 g. (0.099 mole) of 2-hydrazino-4,5-1H-imidazole hydrobromide. Yield 2.5 g. M.p. 258°–60°C (from water/methanol). The free base melts at 265°–8°C (from ethanol/chloroform).

EXAMPLE 9

2-(2,5-Diphenyl-pyrrol-1-yl)amino-4,5-dihydro-1H-imidazole hydrochloride.

By operating substantially as described in Example 7, the title compound is prepared, starting from 25 g. (0.120 mole) of 1,2-dibenzoylethane and 19 g. (0.105 mole) of 2-hydrazino-4,5-dihydro-1H-imidazole hydrobromide. Yield 7.5 g. M.p. 110°–2°C (from ethanol/diethyl ether).

EXAMPLE 10

2-[N-(2,5-Dimethyl-1-pyrrolyl)-N-methyl]amino-4,5-dihydro-1H-imidazole hydrobromide.

The compound is prepared following the same procedure as in Example 1, starting from 13 g. (0.070 mole) of 2-(N-methyl)hydrazino-4,5-dihydro-1H-imidazole hydrobromide and 11 g. (0.093 mole) of 2,5-hexanedione. Yield 4.68 g. M.p. 195°-6°C (from acetone).

EXAMPLE 11

2-[N-Methyl-N-(pyrrol-1-yl)]amino-4,5-dihydro-1H-imidazole-hydrobromide.

According to the procedure described in Example 6 and starting from 6 g. (0.0308) of 2-(1-methyl)hydrazino-4,5-dihydro-1H-imidazole hydrobromide and 3.96 g. (0.030 mole) of 2,5-dimethoxytetrahydrofuran, the title compound is obtained. Yield 4 g. M.p. 199°-201°C (from isopropanol/diisopropyl ether).

EXAMPLE 12

2-(2,5-Dimethyl-pyrrol-1-yl)amino-1,4,5,6-tetrahydropyrimidine hydrobromide.

This compound is prepared through the method described in Example 1, starting from 5 g. (0.0239 mole) of 2-hydrazino-1,4,5,6-tetrahydro-pyrimidine and 15 g. (0.1320 mole) of 2,5-hexanedione. Yield 2.5 g. M.p. 196°-8°C (from isopropanol)

The starting 2-hydrazino-4,5-dihydro-3H-imidazole hydroiodide and hydrobromide were prepared as described by W. G. Finnegan et al. in Journal Org. Chem., 18, 790, 1953. M.p. of the hydroiodide 142°-3°C (from absolute ethanol). M.p. of the hydrobromide 181-3°C (from absolute ethanol).

The starting 2-(N-methyl)hydrazino-4,5-dihydro-1H-imidazole of the compound of Examples 10 and 11 is prepared as hereinbelow described:

To a mixture of 9.2 g. (0.2 mole) of N-methylhydrazine and 30 ml. of absolute ethanol 39.4 (0.186 mole) of 2-ethylmercapto-4,5-dihydro-1H-imidazole hydrobromide prepared as described in Analytica Chemistry, 32, 551, No. 4, 1960, are added dropwise. After one hour and a half reflux the ethylmercaptane which forms is distilled off and the the remaining solution is brought to dryness under vacuum. The residue is twice taken up with a mixture of ethanol and benzene, then triturated with diethyl ether and the resulting ether suspension is filtered. The obtained solid is crystalized from ethanol. Yield 24 g. M.p. 204°-6°C.

In the same way the starting pyrimidine derivative of Example 12 is prepared starting from 2-ethylmercapto-1,4,5,6-tetrahydro-pyrimidine hydrobromide. M.p. 168°-71°C (from ethanol/diethyl ether). The starting 1,4-dicarbonyl compounds of the formula III and their functional derivatives are either commercially available products, or were previously described in the literature, or are prepared as described below. More particularly, those of Example 1, 6, 10, 11, and 12 are commercially available products, the one of Example 3 was described by L. Knorr, Ber., XXVII (1), 1151, 1894, the one of Example 4 was described by R. Willstatter et al., Ber., XLVII (1), 291-320, 1914, the one of Example 5 was described by A. Spassoff, Bull. Soc. Chim. de France, 1658, 1937, the one of Example 8 by J. B. Conant, Journal Am. Chem. Soc. 45, 1303, 1923 and the one of Example 9 is reported by A. Krentzberger, Jour. Org. Chem. 25, 554, 1960.

The compound obtained through the Krentzberger procedure was then nitrated according to known methods to give the starting dicarbonyl compound of Example 7, which is a novel product. M.p. 155°-7°C (from benzene).

3-Methyl-2,5-hexanedione i.e., the starting dicarbonyl substance of Example 2, was prepared according to the procedure described by O. Dann in Ber., 85, 457, starting from 3-chloro-2-butanone, obtained as reported by Justoni, La Chimica e l'Industria, XXIV (3), 89, 1942. B.p. 75°-8°C/14 mmHg.

I claim:

1. A compound of the formula

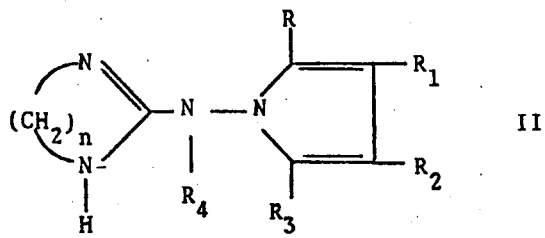

II wherein R, $R_1$, $R_2$, $R_3$ may be the same or different and are independently selected from the class consisting of hydrogen, lower alkyl, carbo-lower alkoxy, phenyl, substituted phenyl, $R_4$ represents hydrogen or lower alkyl, n is 2, and a pharmaceutically acceptable acid addition salt thereof.

2. The compound of claim 1 which is 2-(2,5-dimethyl-pyrrol-1-yl) amino-4,5-dihydro-1H-imidazole and its acid addition salts.

3. The compound of claim 1 which is 2-(2,3,5-trimethylpyrrol-1-yl)amino-4,5-dihydro-1H-imidazole and its acid addition salts.

* * * * *